US006391914B1

(12) United States Patent
Knoll et al.

(10) Patent No.: US 6,391,914 B1
(45) Date of Patent: *May 21, 2002

(54) OPTICALLY ACTIVE AMINOPENTANE DERIVATIVES

(75) Inventors: Joseph Knoll, Budapest (HU); Fumio Yoneda, Matsubara (JP); Hironori Ohde, Matsubara (JP); Masatoshi Sakae, Matsubara (JP); Toshiaki Moto, Matsubara (JP); Takashi Ando, Matsubara (JP); Seiichiro Shimazu, Matsubara (JP); Kazue Takahata, Matsubara (JP)

(73) Assignee: Fujimoto Brothers Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/581,747

(22) PCT Filed: Oct. 15, 1999

(86) PCT No.: PCT/JP99/05729

§ 371 Date: Jun. 16, 2000

§ 102(e) Date: Jun. 16, 2000

(87) PCT Pub. No.: WO00/26204

PCT Pub. Date: May 11, 2000

(30) Foreign Application Priority Data

Oct. 29, 1998 (JP) .......................................... 10-347756

(51) Int. Cl.$^7$ ...................... A61K 31/343; C07D 307/81
(52) U.S. Cl. ........................................ 514/469; 549/467
(58) Field of Search ........................... 514/469; 549/467

(56) References Cited

U.S. PATENT DOCUMENTS 5,589,513 A    12/1996   Magyar et al.
6,214,859 B1    4/2001   Knoll et al.

FOREIGN PATENT DOCUMENTS

| JP | 8-59578 | 3/1996 |
| WO | 88/02254 | 4/1988 |
| WO | 99/07667 | 2/1999 |

*Primary Examiner*—T. A. Solola
(74) *Attorney, Agent, or Firm*—Wenderoth, Lind & Ponack, L.L.P.

(57) ABSTRACT

A novel optically pure (−)-1-(Benzofuran-2-yl)-2-propylaminopentane as represented by the following formula, which contains no (+)-isomer, and the pharmaceutically acceptable acid salt thereof. These compounds have excellent CAE effect (catecholaminergic activity enhancer effect) which is the enhancing action of neurotransmitter catecholamine release, and are useful as psychotropic composition, antidepressants, composition for treating Parkinson's disease and/or Alzheimer's disease.

14 Claims, 2 Drawing Sheets

OPTICALLY ACTIVE AMINOPENTANE DERIVATIVES

This application is a 371 of PCT/JP99/05729 filed Oct. 15, 1999.

BACKGROUND OF THE INVENTION

1. Field of the Invention

The invention relates to a novel optically active aminopentane derivative, (−)-1-(benzofuran-2-yl)-2-propylaminopentane, which contains substantially no (+)-isomer, and to the pharmaceutically acceptable acid salts thereof. These are promising as active compounds of a pharmaceutical composition, especially, psychotropic composition, antidepressant, composition for treating Parkinson's disease and/or Alzheimer's disease.

2. Description of the Related Art

The ethylamine derivatives are known to have various biological actions. Particularly, aromatic ethylamine derivatives are thought to be hopeful as psychotropic composition, because they have the releasing action of displacing catecholamines from their storage places in the central nervous system. However, it is pointed out that these compositions have stimulant-like side effects such as neurotoxicity and abnormal behavior, because they easily cause excess catecholamine release from storage places, i.e. synaptic vesicles and so on. The continuous administration of these compositions, which enhance the excess catecholamine release, induces the decrease of catecholamine receptors. Consequently, the response of patients to these compositions is gradually reduced and no sufficient therapeutic effect can be obtained.

On the other hand, novel phenethylamine derivatives had been disclosed in WO 88/2254 as a psychotropic composition and so on. Considerable attention has been paid to these phenethylamine derivatives, because these showed the catecholaminergic activity enhancer effect (CAE effect), which is a newly discovered action to enhance the catecholamine release due to amplification of the membrane potential dependent exocytosis, and which is different from the above releasing action by displacing catecholamine from their storage [Life Sci., 58, 945–952 (1996)]. However, these compounds did not settle the increase of the intersignal reaction that is an indicator of abnormal behavior in the conditioned avoidance task. Therefore, the development of highly selective CAE drug has been required. Then, we had developed novel compounds enhancing catecholamine release by CAE effect, and found them useful as a psychotropic composition, antidepressants, composition for the treatment of Parkinsons's disease and/or of Alzheimer's disease (patent application No. JP 9/247445).

Organic amine compounds in patent application No. JP 9/247445 are racemic compounds consisting of two equimolar amount of optical isomers (enantiomers), because they have an asymmetric carbon. As for racemic compounds that are mixtures of optical isomers, one of a pair generally showed higher activity than the other. Therefore, optical resolutions of isomers were tried by using the methods preparing the diastereomer salts or derivatives. However, it turned out not to be easy to carry out the optical resolution of racemic compounds in patent application No. JP 9/247445, because of their own flexible substituents.

The purpose of the invention is to obtain the respective optical isomers from organic amine compounds in patent application No. JP 9/247445 by means of the optical resolution, and to find useful remedies from the optical isomers by pharmacological screening. Furthermore, pharmaceutical compositions such as a psychotropic composition, antidepressants, composition for treating Parkinson's disease, and/or Alzheimer's disease, are also the purpose of the invention.

SUMMARY OF THE INVENTION

Following the invention, above purpose of the invention is achieved by novel optically pure (−)-1-(benzofuran-2-yl)-2-propylaminopentane as represented by the following formula and the pharmaceutically acceptable acid salts thereof, and a pharmaceutically acceptable carrier.

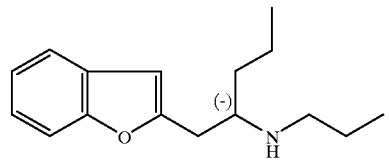

The inventors have examined optical resolution to obtain optically pure isomers from racemic compounds that were psychotropic composition, antidepressants, composition for treating Parkinson's disease and/or Alzheimer's disease. Various methods were tried to obtain optically active compound from the compounds in patent application No. JP 9/247445, and at last, optical resolution was achieved by high performance liquid chromatography method using a chiral column described in example 1. This novel optically active compound or its acid salts were found to show psychotropic and antidepressant actions by excellent CAE effects. Particularly (−)-1-(benzofuran-2-yl)-2-propylaminopentane or the pharmaceutically acceptable acid salts thereof were found to show high activity, and the invention was completed.

No one has expected whether among these compounds (−)-1-(benzofuran-2-yl)-2-propylaminopentane substantially including no (+)-form showed excellent CAE effect, or not. Because a lot of compounds disclosed in patent application No. JP 9/247445, including 1-(benzofuran-2-yl)-2-propylaminopentane, are not open to the public now, and the method of optical resolution for these racemic organic amine compounds and pharmacological actions of optical isomer also have been unknown.

DESCRIPTION OF THE PREFERRED EMBODIMENTS

Figure 1:
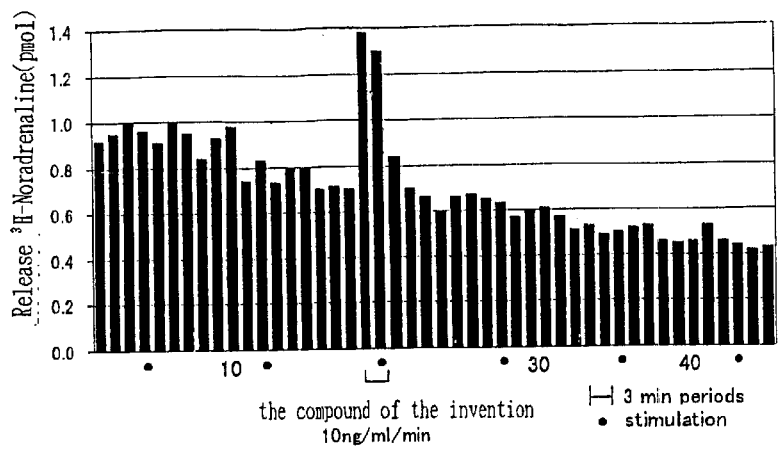
FIG. 1. This figure shows that the compound of the invention enhances noradrenaline, dopamine and serotonin release from isolated rat brain stem by electrostimulation. "⌴" means the treatment of this compound, and "●" means electrostimulation.
Figure 1:
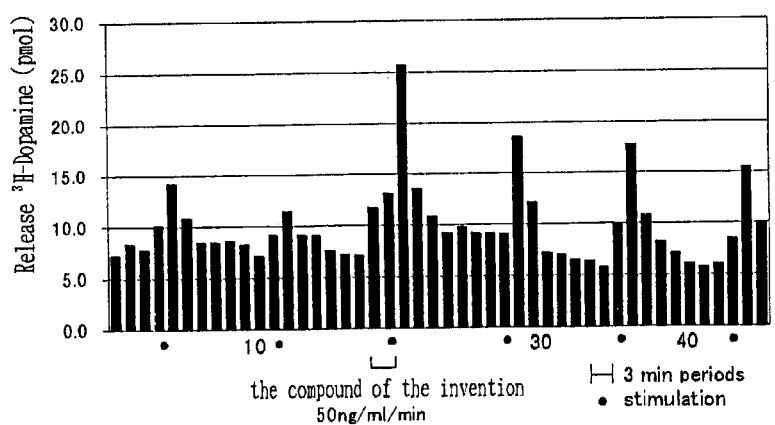
Figure 1:
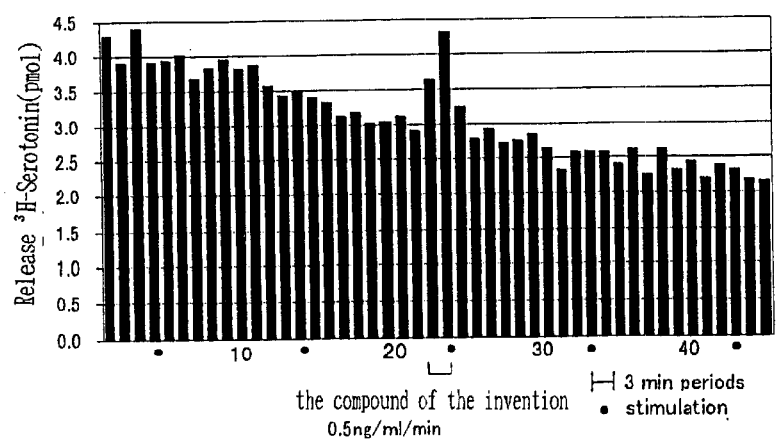

The compound in the invention is (−)-enantiomer of a certain compound disclosed in patent application No. JP 9/247445, and in this specification the sentence "what essentially including no (+)-isomer" means its optical purity to be more than 80% ee, and desirably 90% ee. Pharmacological actions of (−)-1-(benzofuran-2-yl)-2-propylaminopentane, which contains no (+)-isomer substantially, are better than the racemic compounds disclosed in patent application No. JP 9/247445.

We concretely give the salts with inorganic acid, pharmaceutically acceptable which were desirable, such as hydrochloric acid, sulfuric acid, hydrobromic acid, nitric acid, methansulfonic acid and so on, or organic acid such as gluconic acid, tartaric acid, maleic acid, fumaric acid, succinic acid, malic acid, mandelic acid and so on.

The compound in the invention and the acid salts show pharmacological action such as pyschotropic action due to the catecholaminergic activity enhancer effect (CAE effect). In addition, the inventors are able to use them as a composition for the treatment of Parkinson's disease, antidepressants and psychotropic composition.

When measuring catecholamines released from rat brain stem submerged in Krebs' solution during resting or electrostimulating periods, catecholamine release significantly increases with this compound only during electrostimulating period, but not resting. This action of the compound of the invention is much higher than the racemic compounds disclosed in patent application No. JP 9/247445. (+)-Isomer shows the same activity as racemic compound dose. Furthermore, although the administration with a catecholamine depletor, tetrabenazine, reduced learning ability of rats, the compound of the invention shows a significant improvement in the learning ability which is scored as conditioned avoidance reflexes, in lower doses than (+)-isomer or racemic compound.

These experiments made it clear that the compound of the invention has the catecholaminergic activity enhancer effect, which enhances the exocytosis due to stimulation related to active potential and transmitter release i.e. an increase of intracellular $Ca^{2+}$ concentration in neuron. Furthermore, this physiological action, without abnormal behavior and amine depletion in catecholaminergic nerve terminal, is different from the releasing action of the known composition to displace catecholamine.

When using the compounds of the invention or the pharmaceutical acceptable acid salts thereof as above medicine, these are orally or parenterally administered as tablets, powders, granules, capsules, syrups, injections or the like. Although used dose is various, and depends on each symptom, age, body weight and so on, the adult oral dose for these compounds is usually between 0.1 and 100 mg/day. In addition, they are administered once or several times a day.

The compound of the invention is explained in more detail in the following Examples. However, the Examples are merely illustrative and should not be construed to limit the spirit and scope of the claims.

EXAMPLE 1

Preparation of (−)-1-(benzofuran-2-yl)-2-propylaminopentane hydrochloride

Optical resolution was carried out by HPLC method under the following conditions. 115 µl of 40.8 mg/ml (±)-1-(benzofuran-2-yl)-2-propylaminopentane hydrochloride (racemic compound) was directly injected into the HPLC.

HPLC: LC-6AD, Shimadzu, Kyoto, Japan

Column: CHIRALPACK AD 20 mmφ X 250 mm (DAICEL)

Mobile phase: hexane:isopropanol:trifluoroacetic acid= 100:2:0.1

Flow rate: 12.0 mL/min

Detector: SPD-10A type UV/VIS detector (280 nm), Shimadzu, Kyoto, Japan

Temperature: room temperature

Oil of (−)-1-(benzofuran-2-yl)-2-propylaminopentane was dissolved in anhydrous ether, and added to ether solution saturated with hydrochloride to convert hydrochloride salt.

Melting point: 165.0–166.0° C.

IR: 3425, 2970, 2870, 2780, 2735, 2690, 2520, 2430, 1605, 1590, 1472, 1455, 1255, 1167, 942, 805, 770, 760 $cm^{-1}$

Elementally analysis: as $C_{16}H_{23}NO \cdot HCl$ Calculated C: 68.19, H: 8.58, N: 4.97 (%) Found C: 68.07, H: 8.48, N: 4.98 (%)

Optical purity: 93% ee

Specific rotation:

$$[\alpha]_D^{20} = -4.08 (c = 4.0, \text{methanol})$$

REFERENCE EXAMPLE

Preparation of (+)-1-(benzofuran-2-yl)-2-propylaminopentane hydrochloride [(+)-form]

Oil of (+)-1-(benzofuran-2-yl)-2-propylaminopentane obtained in example 1 was dissolved in anhydrous ether, and added to ether solution saturated with hydrochloride to convert hydrochloride salt.

Melting point: 170.0–171.0° C.

IR: 3425, 2970, 2870, 2790, 2735, 2700, 2515, 2425, 1607, 1590, 1472, 1455, 1250, 1175, 945, 802, 770, 760 $cm^{-1}$

Elementally analysis: as $C_{16}H_{23}NO \cdot HCl$ Calculated C: 68.19, H: 8.58, N: 4.97 (%) Found C: 67.90, H: 8.44, N: 4.98 (%)

Optical purity: 100% ee

Specific rotation:

$$[\alpha]_D^{20} = +4.01 (c = 4.0, \text{methanol})$$

The results of pharmacological studies are shown as follows.

EXAMPLE 2

Measurement of Biogenic Amines Released From the Rat Brain Stem by Electrostimulation The method described in Life Sci., 58, 2101–2114 (1996) was used. Male rats weighing 280–350 g were stunned by a blow on the back of their head, the brain stem (average weight about 800 mg) was isolated and soaked in oxygenated (95% $O_2$ and 5% $CO_2$) Krebs' solution at 37° C. for 30 min. Thereafter, 20 µL of the $^3H$-noradrenaline solution (1-[7,8-$^3H$]-noradrenaline; specific activity: 30–50 Ci/mmol; Amersham) was added to the preparation and 45 min were allotted for uptake. The composition of Krebs' solution (mmol/L) was as follows: $Na^+$ 137.4; $K^+$ 5.9, $Ca^{2+}$ 2.5, $Mg^{2+}$ 1.2, $Cl^-$ 120.2, $H_2PO_4^-$ 1.2, $HCO_3^-$ 25.0, $SO_4^{2-}$ 1.0 and glucose 11.5, ascorbic acid 0.3 and EDTA-2Na 0.03. During the period for the uptake of labeled transmitter, pargyline (12 mmol) was present in Krebs' solution to inhibit MAO activity.

After uptake of $^3H$-noradrenaline, the brain stem was fixed in organ bath containing 5 ml of Krebs' solution (37° C.). The brain was then washed at the rate of 8 mL/min with oxygen saturated Krebs' solution containing 0.03 mmol/L of cocaine. After 100 min, perfusion rate was reduced by 4 mL/min and Krebs' solution was modified to contain also 0.05 mmol/L of corticosterone. The experiment was carried out in the presence of cocaine and corticosterone (under this condition, 86% of $^3$H-noradrenaline is not metabolized nor taken up into both neuron and the other cells). Fractionation of perfusate was carried out every 3 min. Adding 1 mL perfusate to 5 mL Aquasafe 300 P (Zinsser), and the amount of $^3$H-noradrenaline released during each 3-min period was determined using scintillation counter (Beckman LS-900). The amounts of serotonin and dopamine were also determined in the same manner. The brain stem was stimulated with rectangular pulses (3 Hz, 1 ms, 60 V) for 3 min. At the beginning of the experiment, the three resting periods of fraction were proceeded prior to the first stimulation. Thereafter it was allotted seven resting periods of fraction between stimulation. The compounds of the invention were solved in perfusate buffer and the solutions of 0.5, 1, 2.5 and 5 μg/mL were prepared. The buffer containing the compounds of the invention was perfused for 3 min before electrostimulation. The results were shown in FIG. 1.

As shown in FIG. 1, the compound of the invention was confirmed to enhance noradrenaline, serotonin and dopamine release by the increase of the exocytosis, when electrostimulation was given to the neuronal cells. Furthermore, the effects of the compound of the invention were found out in lower dose than (+)-form and racemic compound, as shown in Table 1.

TABLE 1.

Minimum dose (μg/mL) of the compound of the invention causing to release noradrenaline, dopamine and serotonin from electric-stimulated brain stem.

|  | The compound of the invention | (+)-Isomer | Racemic compound |
| --- | --- | --- | --- |
| Noradrenaline | $1 \times 10^{-2}$ | $5 \times 10^{-1}$ | 5 |
| Dopamine | $5 \times 10^{-2}$ | 5 | N.D. |
| Serotonin | $5 \times 10^{-4}$ | 10 | 1 |

EXAMPLE 3

The Effects on Conditioned Avoidance Task in the Shuttle Box

The method described in Life Sci., 58, 817–827 (1996) was used. The effects on conditioned avoidance reflex (CARs) were analyzed in the shuttle box using male and female rats (weighing 200–220 g) whose learning abilities were reduced by the administration of tetrabenazine. The instrument was constructed, according to the device described in Psychopharmacologia 10, 1–5 (1966). The male and female rats (weighing 200–220 g) were trained to cross the barrier under a conditioned stimulus. (CS, light flash and buzzer sounds). If they failed to do so, they were punished with a footshock (1 mA) that was an unconditioned stimulus (US). If the rats failed to respond within 5 sec to US, it was noted as an escape failure (EF). In addition, the unconcerned performance to this condition was noted as an intersignal reaction (IR). The rats were trained with 100 trials a day for 5 days. Each trial was carried out with 15-sec intertrial interval. Tetrabenazine saline solution was subcutaneously administered at a dose of 1 mg/kg 1 hr before the test. Then the solution of the compounds of the invention was administered at the doses of 1, 2, 2.5 and 5 mg/kg, s.c., simultaneously with tetrabenazine. The numbers of CARs, EFs and IRs were automatically counted and analyzed using one-way analysis of variance (ANOVA). The results were shown in FIG. 2.

Figure 2:
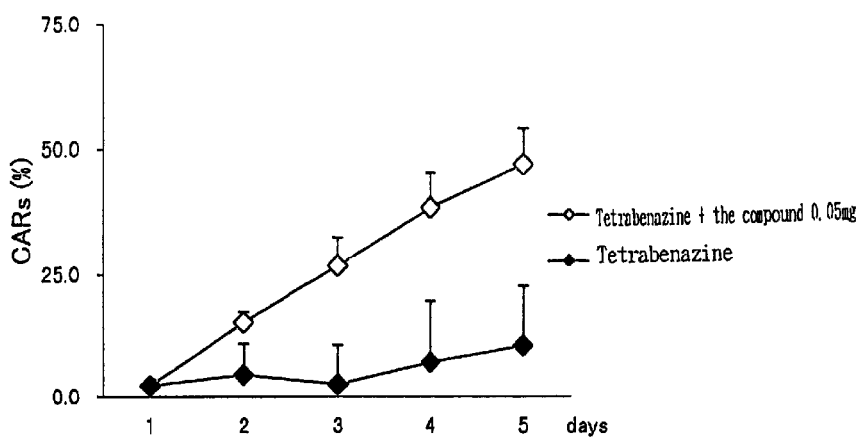
FIG. 2. This figure shows the efficacy of the compound of the invention on reduced learning ability of rats administered with tetrabenazine, when using shuttle box task.
Figure 2:
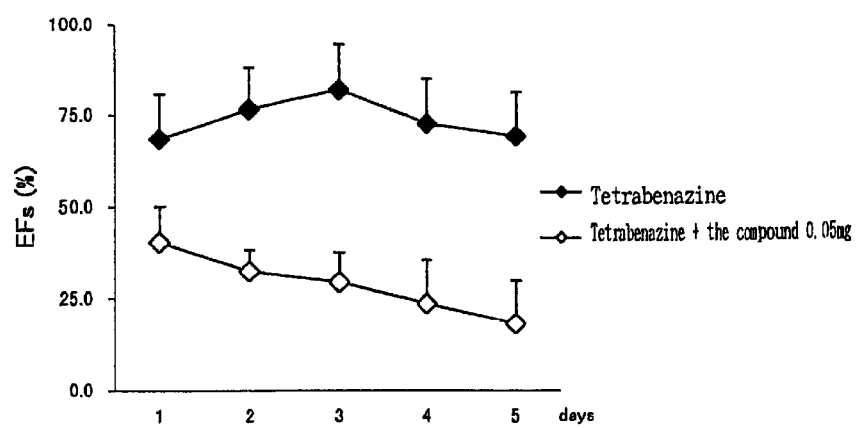
Figure 2:
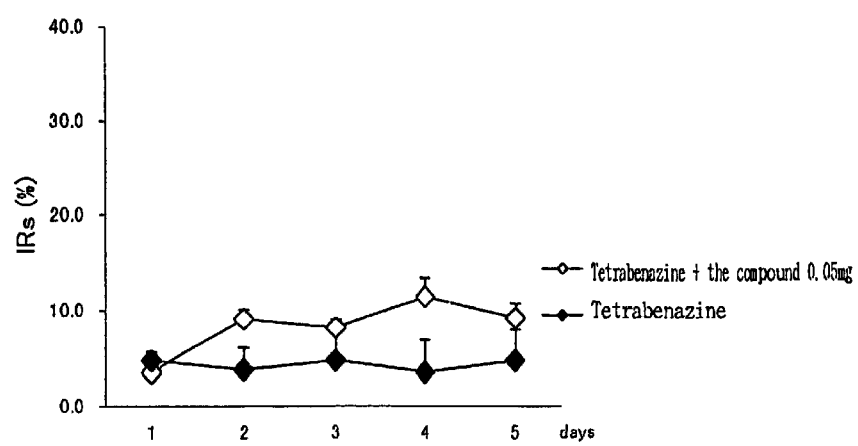

As shown in FIG. 2, the compound of the invention significantly improved the reduced learning function of the rats administered with tetrabenazine. The effect of the compound of the invention was observed in much lower dose than (+)-isomer or racemic compound, as shown in Table 2. It is considered that these compounds may have antidepressant effects, because EF significantly decreased. Furthermore, the compound of the invention did not significantly change IRs that mean excitement under no conditioning stimulation and related to abnormal behavior. Therefore, the compound has no stimulant-like excitement.

TABLE 2.

Minimum dose (mg/kg) of the compound of the invention, (+)-form or racemic compound to cause conditioned avoidance reflexes (CARs) in tetrabenazine-treated rats in shuttle box.

| The compound of the invention | (+)-Isomer | Racemic compound |
| --- | --- | --- |
| $5 \times 10^{-2}$ mg | 2.5 mg | 1 mg |

EXAMPLE 4

Measurement of Biogenic Amines Released From Brain Tissue

The method described in Life Sci., 56, 611–620 (1995) was used. After Wistar rats were decapitated, appropriate brain tissues (striatum, substantia nigra, tuberculum olfactorium, locus coeruleus and raphe) were isolated quickly and soaked in oxygenated (95% $O_2$ and 5% $CO_2$) Krebs' solution at 37° C. The composition of Krebs' solution (mmol/L) was as follows: NaCl 111, KCl 4.7, $CaCl_2$ 2.5, $MgSO_4$ 1.64, $NaHCO_3$ 25, $KH_2PO_4$ 1.2, glucose 12 mg/L ascorbic acid and 20 mg/l EDTA-2Na. The preparations, submerged in one organ bath, were as follows: 1) four pieces of striatum (each halved), 2) four pieces of substantia nigra, 3) four pieces of tuberculum olfactorium, 4) eight pieces of locus coeruleus, 5) eight pieces of raphe. After incubating the tissue for 20 min, the Krebs' solution was exchanged. After the tissue was submerged for 20 min in Krebs' solution containing the compounds of the invention, the biogenic amine released during this period was quantified. The compounds of the invention, the (+)-isomer, the racemic compound and control compound, were respectively dissolved in saline, and subcutaneously administered 30 min before dissection of the brain samples. In the case of noradrenaline and dopamine, samples were purified on microcolumns (BDH Chemicals Ltd.) filled with 60 mg of alumina according to the method described in J. Pharmacol. Exp. Ther., 138, 360–372 (1962). In the case of serotonin, samples were purified on 15 mg Sephadex G-10 microcolumns (Pharmacia). Dopamine, noradrenaline and serotonin were quantified by high performance liquid chromatography (Waters 746 data module) with electrochemical detection (Waters 460 electrochemical detector). Waters Resolve 5μ Spherical $C_{18}$ 3.9×150 mm column was used as separating column and triethylamine-phosphate buffer (pH 5.2) containing 200/mg/L octaine sulfonate sodium and 18 mg/L EDTA-2Na with 6% acetonitrile, was used as mobile phase. The amount of appropriate amine released for 20 min was noted as nmol/g tissue. The differences among means were tested using Student's t-test. Significant level was set at $P<0.05$. The results are shown in Table 3.

Although the compounds of the invention, the (+)-isomer and racemic compound respectively increased biogenic amine release, the compounds of the invention showed the efficacy in lower concentration than the (+)-form and racemic compound, as shown in Table 3.

times volumes of ice-cold 0.35 mol/L sucrose (pH 7.4) using glass homogenizer with Teflon pestle, which was revolted by

TABLE 3

Amount of biogenic amines released from brain tissues (nmol/g · tissue. 20 min.)

| | Dose | Dopamine | | | Noradrenaline | Serotonin |
|---|---|---|---|---|---|---|
| | mg/kg | Striatum | Substantia Nigraia | Tuberculum Olfactorium | Locus Coeruleus | Raphe |
| Saline | — | 4.5 ± 0.15 | 6.8 ± 0.18 | 4.9 ± 0.15 | 4.7 ± 0.10 | 0.391 ± 0.02 |
| The compound of the invention | 0.0001 | 4.7 ± 0.14 | 14.8 ± 0.36**** | 7.2 ± 0.23**** | 6.6 ± 0.10*** | 1.040 ± 0.03*** |
| | 0.0005 | 4.8 ± 0.16 | 13.8 ± 0.23**** | 6.7 ± 0.08**** | 15.4 ± 0.55**** | 0.914 ± 0.03*** |
| | 0.0025 | 5.7 ± 0.19*** | 13.1 ± 0.21**** | 6.9 ± 0.31**** | 3.9 ± 0.05** | 0.421 ± 0.03 |
| | 0.0500 | 6.5 ± 0.09**** | 10.9 ± 0.11**** | 7.7 ± 0.19**** | 4.3 ± 0.25 | 0.457 ± 0.01 |
| (+)-Isomer | 0.0005 | 4.4 ± 0.13 | 13.8 ± 0.25**** | 6.7 ± 0.06**** | 10.3 ± 0.35*** | 1.785 ± 0.01**** |
| | 0.0025 | 4.4 ± 0.10 | 8.4 ± 0.14**** | 4.8 ± 0.25 | 7.4 ± 0.15*** | 1.138 ± 0.05*** |
| | 0.0500 | 4.4 ± 0.17 | 7.1 ± 0.24 | 4.8 ± 0.18 | 4.4 ± 0.10 | 0.642 ± 0.02** |
| | 0.1000 | 5.8 ± 0.21*** | 15.9 ± 0.25**** | 7.3 ± 0.20**** | 5.6 ± 0.25 | 0.381 ± 0.01 |
| Racemic compound | 0.0100 | 5.3 ± 0.14*** | 6.6 ± 0.04*** | 6.5 ± 0.20*** | 4.3 ± 0.20 | 0.457 ± 0.04 |

**P < 0.02
***P < 0.01
****P < 0.001

EXAMPLE 5

Effect on the Monoamine Oxidase Type-B (MAO-B)

After male C57B1/6 mice were decapitated, the whole brain was isolated immediately. The brain samples were weighed, and homogenized in 0.2 mol/L potassium phosphate buffer (pH 7.5) containing 1.0% EDTA-2Na by homogenizer. After the homogenate was centrifuged at 2,000 RPM for 20 min, the supernatant was centrifuged at 18,000 RPM (40,000 g) for 30 min. The pellet was resuspended, and further centrifuged in the same manner. Thereafter, the pellet was resuspended in the above buffer to be enzyme solution. All procedure was carried out at 4° C.

$^{14}$C-Labeled substrate ($^{14}$C-phenylethylamine) and enzyme solution from mice are mixed in test tube, incubated for 30 min at 37° C., and stopped the reaction with 20 µL of 6 mol/L Hcl. The reaction product was extracted with toluene-ethylacetate (1:1), and the radioactivity was measured using scintillation counter. Then, MAO-B inhibitory activity was calculated. Results are shown in Table 4. Inhibitory activity of each compound in $10^{-5}$ mol/L was below 50%, as shown in Table 4. This suggested that the compound of the invention had no MAO-B inhibitory action.

TABLE 4.

Mice brain MAO-B inhibitory effects in the concentration of $10^{-5}$ mol/L.

| | Inhibitory activity |
|---|---|
| The compound of the invention | 4.7% |
| (+)-Isomer | 1.7% |
| Racemic compound | 22.9% |

EXAMPLE 6

The Affinities to Receptors of $\alpha_1$, $\alpha_2$, $D_1$, $D_2$, 5-$HT_1$ and 5-$HT_2$ The receptor solution was prepared as follows. After the rats were decapitated, brain was immediately isolated and weighed. Thereafter, brain samples were homogenized in ten motors. The homogenate was centrifuged at 4° C. at 900×g for 10 min and the supernatant was, furthermore, recentrifuged at 4° C. at 22,000×g for 20 min. The precipitate was suspended with addition of 5 mmol/L phosphate buffer solution (pH 7.4). After the suspension was incubated at 37° C. for 30 min, the suspension was recentrifuged at 4° C. at 20,000×g for 20 min. The precipitate was resuspended in 10 ml of 5 mmol/L phosphate buffer solution (pH 8.0) to be receptor solution.

$^3$H-prazocin was used as a ligand. 0.25 nmol/L of $^3$H-prazocin, the compounds of the invention and the receptor solution, which were respectively prepared in 5 mmol/L phosphate buffer (pH 8), were put in tube and the mixture was incubated at 25° C. for 90 min. In addition, the nonspecific binding was evaluated with binding value of $^3$H-prazocin in the presence of 0.1 µmol/L prazocin. The binding assay was carried out as follows. After $^3$H-prazocin (binding type: B) bound to receptor, only the binding type of $^3$H-prazocin was collected using B/F separator (Brandel, USA) with glass fiber filter (pore size: 0.5 µm Whatman GF/C), and free type of prazocin (free type: F) was removed. Glass-fiber filter, absorbing the binding type of $^3$H-prazocin, was washed with ice-cold saline solution and transferred to vial. After 10 ml of scintillation cocktail was put in it, the radioactivity was measured. Affinity of the compounds of the invention to $\alpha_1$ receptor was evaluated from the inhibition rate of binding between $\alpha_1$ receptor and the ligand.

Affinities of the compounds of the invention to receptors of $\alpha_2$, $D_1$, $D_2$, 5-$HT_1$ and 5-$HT_2$ were respectively determined in the same manner, while used 0.7 nmol/L $^3$H-rauwolscine, 1.4 nmol/L $^3$H-SCH-23390, 2.0 nmol/L spiperone, 2 nmol/L $^3$H-5-HT and 0.5 nmol/L $^3$H-ketanserin as each ligands. In addition, 1 µmol/L yohimbine, 10 µmol/L (+)-butaclamol, 10 µmol/L haloperidol, 10 µmol/L 5-HT and 1 µmol/L ketanserin were respectively used as their displacers. If affinity of a certain compound to a certain receptor is high, the binding between radio ligand and the receptor is inhibited. If the concentration of a certain compound, that is necessary for 50% inhibition of binding between ligand and receptors, is higher than $10^{-6}$ mol/L, it is generally considered that its compound do not have the activity enough to show physiological activity. The result was shown in Table 5.

The compounds of the invention, (+)-isomer and the racemic compound did not show any affinity that was necessary to exhibit physiological action, as shown in Table 5.

TABLE 5

| | Affinity to receptors* | | | | | |
|---|---|---|---|---|---|---|
| | $\alpha_1$ | $\alpha_2$ | $D_1$ | $D_2$ | 5-HT$_1$ | 5-HT$_2$ |
| The compound of the invention | >10$^{-5}$ | 3.1 × 10$^{-6}$ | >10$^{-5}$ | >10$^{-5}$ | >10$^{-5}$ | 1.0 × 10$^{-5}$ |
| (+)-isomer | >10$^{-5}$ | 2.6 × 10$^{-6}$ | >10$^{-5}$ | >10$^{-5}$ | >10$^{-5}$ | >10$^{-5}$ |
| Racemic compound | >10$^{-5}$ | 1.0 × 10$^{-6}$ | >10$^{-5}$ | >10$^{-5}$ | >10$^{-5}$ | 2.0 × 10$^{-5}$ |

*Concentration (mol/L) showing 50% inhibition between each ligands and receptor

The results of safety tests were shown as follows.

EXAMPLE 7

Toxicity Screening Using Primary Cultured Hepatocyte

The hepatocytes was prepared from rat liver using collagenase perfusion method and the cell suspension containing 5×10$^5$ cells/mL were prepared. After cultivation for 24 hr, the medium was changed to the William's Medium E (GIBCO ERL) containing 10 or 100 μmol/L of the compounds of the invention. After cultivation for 24 hr, the activity of lactatedehydrogenase (LDH) released into the medium was measured.

In results, 100 μmol/L of the compound of the invention slightly increased LDH release, but 10 μmol/L not increase, as shown in Table 6.

TABLE 6

Percent control of LDH release from primary cultured hepatocyte by the compound of the invention, the (+)-form or racemic compound.

| | 100 μmol/L | 10 μmol/L |
|---|---|---|
| The compound of the invention | 126.42 ± 8.04* | 104.94 ± 4.96 |
| (+)-Isomer | 116.72 ± 6.91 | 124.41 ± 12.54 |
| Racemic compound | 112.10 ± 36.98 | 90.28 ± 2.85 |

EXAMPLE 8

Toxicity Test in Mice in the Single Administration

The general symptoms of the mice were observed every day for two weeks after the administration of the compound of the invention as the dose of 100 mg/kg.p.o. In results, every three numbers of mice survived.

What is claimed is:

1. A compound (−)-1-(Benzofuran-2-yl)-2-propylaminopentane as represented by the following formula and the pharmaceutically acceptable acid salts thereof

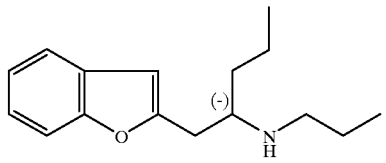

2. The compound according to claim 1, wherein the compound (−)-1-(Benzofuran-2-yl)-2-propylaminopentane has an optical purity of more than 80% ee.

3. A pharmaceutical composition comprising one or more compounds of claim 1, as an active ingredient, and a pharmaceutically acceptable carrier or diluent.

4. A method for enhancing catecholamine release in central nervous system comprising administering, as an active ingredient, a therapeutically effective amount of one or more compounds of claim 1.

5. A method for treating psychotropic diseases comprising administering, as an active ingredient, a therapeutically effective amount of one or more compounds of claim 1.

6. A method for treating depression comprising administering, as an active ingredient, a therapeutically effective amount of one or more compounds of claim 1.

7. A method for treating Parkinson's disease comprising administering, as an active ingredient, a therapeutically effective amount of one or more compounds of claim 1.

8. A method for treating Alzheimer's disease comprising administering, as an active ingredient, a therapeutically effective amount of one or more compounds of claim 1.

9. The pharmaceutical composition according to claim 3, wherein the compound (−)-1-(Benzofuran-2-yl)-2-propylaminopentane has an optical purity of more than 80% ee.

10. A method for enhancing catecholamine release in central nervous system comprising administering a therapeutically effective amount of the pharmaceutical composition of claim 9.

11. A method for treating psychotropic diseases comprising administering a therapeutically effective amount of the pharmaceutical composition of claim 9.

12. A method for treating depression comprising administering a therapeutically effective amount of the pharmaceutical composition of claim 9.

13. A method for treating Parkinson's disease comprising administering a therapeutically effective amount of the pharmaceutical composition of claim 9.

14. A method for treating Alzheimer's disease comprising administering a therapeutically effective amount of the pharmaceutical composition of claim 9.

* * * * *